(12) United States Patent
Choi et al.

(10) Patent No.: US 9,339,557 B2
(45) Date of Patent: May 17, 2016

(54) PHOTOSENSITIZER-METAL NANOPARTICLE COMPLEX AND COMPOSITION CONTAINING THE COMPLEX FOR PHOTODYNAMIC THERAPY OR DIAGNOSIS

(75) Inventors: Yong-Doo Choi, Gyeonggi-do (KR); Bo-Seung Jang, Gyeonggi-do (KR); In-Hoo Kim, Gyeonggi-do (KR); Jin-Young Park, Gyeonggi-do (KR)

(73) Assignee: NATIONAL CANCER CENTER, Gyeonggi-Do (KR)

( * ) Notice: Subject to any disclaimer, the term of this patent is extended or adjusted under 35 U.S.C. 154(b) by 1458 days.

(21) Appl. No.: 12/665,013

(22) PCT Filed: Oct. 8, 2009

(86) PCT No.: PCT/KR2009/005763
§ 371 (c)(1),
(2), (4) Date: Dec. 16, 2009

(87) PCT Pub. No.: WO2011/043502
PCT Pub. Date: Apr. 14, 2011

(65) Prior Publication Data
US 2011/0293728 A1    Dec. 1, 2011

(51) Int. Cl.
| | | |
|---|---|---|
| *A61K 51/00* | (2006.01) |
| *A61K 49/00* | (2006.01) |
| *A61B 5/00* | (2006.01) |
| *A61K 39/00* | (2006.01) |
| *C07D 345/00* | (2006.01) |
| *C07B 47/00* | (2006.01) |
| *C07D 225/00* | (2006.01) |
| *C07D 295/00* | (2006.01) |
| *A61K 47/48* | (2006.01) |
| *A61K 41/00* | (2006.01) |
| *C12N 9/00* | (2006.01) |

(52) U.S. Cl.
CPC ....... *A61K 47/48861* (2013.01); *A61K 41/0071* (2013.01); *A61K 47/48246* (2013.01); *A61K 49/0017* (2013.01); *A61K 49/0065* (2013.01)

(58) Field of Classification Search
CPC ............. A61K 47/488861; A61K 47/48246; A61K 49/0017; A61K 49/0065; A61K 41/0071
USPC .......... 424/1.11, 9.6, 9.61, 178.1; 540/1, 145, 540/450; 428/402; 530/330
See application file for complete search history.

(56) References Cited

U.S. PATENT DOCUMENTS

2009/0016962 A1    1/2009   Fukumura et al.

FOREIGN PATENT DOCUMENTS

| KR | 10-2003-0038814 | 5/2003 |
| KR | 10-2006-0135719 | 12/2006 |
| WO | WO 2004/085387 | * 10/2004 |
| WO | WO 2007/023398 | * 3/2007 |

OTHER PUBLICATIONS

Liu et al., "In Vitro Targeted Photodynamic Therapy with a Pyropheophorbide-a Conjugated Inhibitor of Prostate-Specific Membrane Antigen", The Prostate 69: 585-594, Department of Chemistry, Washington State University, Pullman, Washington, 2009, Wiley Liss, Inc.
Bechet et al., "Nanoparticles as vehicles for delivery of photodynamic therapy agents," *Trends in Biotechnology*, 26(11), pp. 612-621 (Sep. 2008).
Law et al., "Proteolysis: A biological process adapted in drug delivery, therapy, and imaging," *Bioconjugate Chemistry*, 20(9), pp. 1683-1695 (Sep. 2009).
Park et al., "New Generation of Multifunctional Nanoparticles for Cancer Imaging and Therapy," *Advanced Functional Materials*, 19(1), pp. 1553-1566 (May 2009).
Martina E. Wieder et al., "Intracellular photodynamic therapy with photosensitizer-nanoparticle conjugates: cancer therapy using a 'Trojan horse'", *Photochemical & Photobiological Sciences*, 2006, vol. 5, pp. 727-734.
Kyeongsoon Park et al., "New Generation of Multifunctional Nanoparticles for Cancer Imaging and Therapy", *Advanced Functional Materials*, 2009, vol. 19, pp. 1553-1566.

* cited by examiner

*Primary Examiner* — Sharmila G. Landau
*Assistant Examiner* — Shannon Janssen
(74) *Attorney, Agent, or Firm* — Michel Morency; Foley & Lardner LLP (57) ABSTRACT

Provided are a photosensitizer-metal nanoparticle complex and a composition for photodynamic therapy or diagnosis having the same. The complex includes a photosensitizer, a metal nanoparticle, and a backbone linking the photosensitizer with the metal nanoparticle. The backbone has a polypeptide substrate capable of being specifically degraded by a protease. When the complex is administered to a patient, fluorescence and production of reactive oxygen species from the conjugated photosensitizers are inhibited in normal tissues due to the resonance energy transfer between the photosensitizer and metal nanoparticles, but in tumor tissues, fluorescence and production of reactive oxygen species from the released photosensitizers are activated, thereby effectively destroying the tumor tissues. In addition, the selective fluorescence in the tumor tissues can further improve accuracy of tumor diagnosis using the protease-activatable photosensitizer-metal nanoparticle complex.

8 Claims, 6 Drawing Sheets

| Detector A - 1 (220nm) | | | | | |
|---|---|---|---|---|---|
| Pk # | Retention Time | Area | Area % | Height | Height % |
| 1 | 8.075 | 23884 | 0.382 | 3568 | 0.561 |
| 2 | 8.158 | 36059 | 0.577 | 4287 | 0.674 |
| 3 | 8.492 | 6166717 | 98.699 | 624703 | 98.193 |
| 4 | 8.892 | 21324 | 0.341 | 3642 | 0.572 |
| Totals | | 6247984 | 100.000 | 636200 | 100.000 |

HT1080 (MMP2 +)

Fig. 10

BT20 (MMP2 -)

PHOTOSENSITIZER-METAL NANOPARTICLE COMPLEX AND COMPOSITION CONTAINING THE COMPLEX FOR PHOTODYNAMIC THERAPY OR DIAGNOSIS

RELATED APPLICATIONS

This application is the U.S. National Stage of International Application No. PCT/ KR2009/005763, filed Oct. 8, 2009. The entire contents of the above applications are incorporated herein by reference.

SEQUENCE LISTING

The instant application contains a Sequence Listing which has been submitted electronically in ASCII format and is hereby incorporated by reference in its entirety. Said ASCII copy, created on Sep. 8, 2014, is named 097088-0106_SL.txt and is 4,449 bytes in size.

TECHNICAL FIELD

The present invention relates to a photosensitizer, and more particularly, to a photosensitizer-metal nanoparticle complex and a composition for photodynamic therapy and diagnosis containing the same.

BACKGROUND

Photodynamic therapy using a photosensitizer has attracted attention as a form of therapy capable of overcoming sequelae of cancer and side effects of conventional cancer treatments such as surgery, radiation therapy, and drug therapy.

The photosensitizer is excited by light radiation of a specific wavelength, and reacts with a surrounding substrate or oxygen, thereby producing reactive oxygen species, resulting in apoptosis or necrosis of surrounding tumor cells.

However, when a photosensitizer-administered patient is exposed to light, the photosensitizer currently used for cancer treatment causes a side effect of skin photosensitivity in which the photosensitizer non-specifically accumulated in skin or eyes of the patient is excited thereby kill normal cells of the skin or eyes.

SUMMARY

The present invention is directed to a photosensitizer-metal nanoparticle complex, which allows a photodynamic reaction to more selectively take place in a target infected area to reduce a side effect, and a composition for photodynamic therapy or diagnosis containing the same.

One aspect of the present invention provides a photosensitizer-metal nanoparticle complex. The complex includes a photosensitizer, a metal nanoparticle, and a backbone linking the photosensitizer with the metal nanoparticle. The backbone includes a polypeptide substrate capable of being specifically degraded by a protease.

Another aspect of the present invention provides a composition for photodynamic therapy or diagnosis. The composition includes a photosensitizer-metal nanoparticle complex and a pharmaceutically available carrier.

According to the present invention, in normal tissues, a photosensitizer-metal nanoparticle complex has a photosensitizer linked with a metal nanoparticle by a backbone, thereby inhibiting fluorescence and production of reactive oxygen species. However, in tumors in which a protease is overexpressed, a polypeptide in the backbone is specifically degraded. Thus, the photosensitizer is separated from the metal nanoparticle, so that the fluorescence and production of reactive oxygen species can be activated. As a result, a photosensitive reaction can be inhibited in normal tissues, and tumor tissues can be effectively destroyed. In addition, the selective fluorescence in the tumor tissues can increase accuracy of tumor diagnosis using the complex.

Effects of the present invention will not be limited to the above-mentioned effects, and other effects, which are not described herein, will be clearly understood from the accompanying claims by those ordinarily skilled in the art.

DETAILED DESCRIPTION

Hereinafter, exemplary embodiments of the present invention will be described in detail. However, the present invention is not limited to the exemplary embodiments disclosed below, but can be implemented in various types. Therefore, the present exemplary embodiments are provided for complete disclosure of the present invention and to fully inform the scope of the present invention to those ordinarily skilled in the art.

Photosensitizer-Metal Nanoparticle Complex

Figure 1:
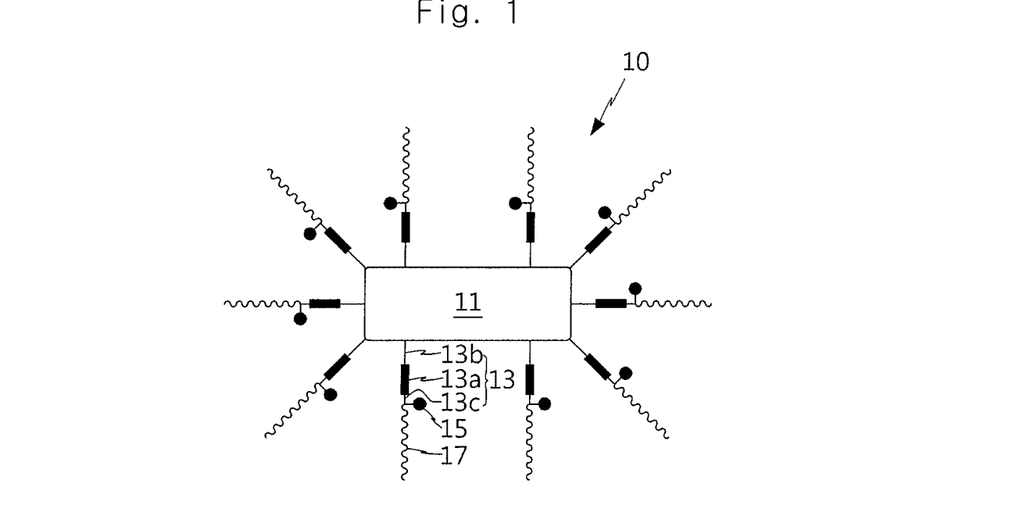
FIG. 1 is a schematic view of a photosensitizer-metal nanoparticle complex according to an exemplary embodiment of the present invention.

FIG. 1 is a schematic view of a photosensitizer-metal nanoparticle complex according to an exemplary embodiment of the present invention.

Referring to FIG. 1, a photosensitizer-metal nanoparticle complex 10 according to an exemplary embodiment of the present invention includes a metal nanoparticle 11, a photosensitizer 15, and a backbone 13 linking the metal nanoparticle 11 with the photosensitizer 15.

The backbone 13 includes a polypeptide substrate 13a capable of being specifically degraded by a specific enzyme relating to a disease, for example, a protease which is overexpressed in tissues having a disease such as a tumor. In one example, the tumor may be composed of proliferating cells.

Examples of such a protease include cathepsins, matrix metalloproteinases (MMPs), membrane-type MMPs, collagenases, gelatinases, stromelysins, urokinase-type plasminogen activators (uPAs), caspases, viral proteases, HIV proteases, HSV proteases, gelatinases, urokinases, secretases, endosomal hydrolases, prostate-specific antigens (PSA), plasminogen activators, cytomegalovirus (CMV) proteases, and thrombins. Specifically, the cathepsins may include cathepsin A, cathepsin B, cathepsin D, cathepsin H, cathepsin K, cathepsin L or cathepsin S, and the MMPs may include MMP1, MMP2, MMP3, MMP7, MMP8, MMP9, MMP10, MMP11, MMP12, or MMP13.

The polypeptide substrate 13a may include an amino acid sequence such as RPLALWRS (SEQ ID NO: 1), GGLGQRGRSANAILE (SEQ ID NO: 2), GVSQNYPIVG (SEQ ID NO: 3), LVLASSSFGY (SEQ ID NO: 4), PLGMWSR (SEQ ID NO: 5), PGNWT (SEQ ID NO: 6), PAGLLGC (SEQ ID NO: 7), LGGSGRSANAILE (SEQ ID NO: 8), RR, RRG, GPICFFRLG (SEQ ID NO: 9), HSSKLQG (SEQ ID NO: 10), PIC(Et)FF (SEQ ID NO: 11), HSSKLQ (SEQ ID NO: 12), P(L/Q)G(I/L)AG (SEQ ID NO: 13), GVVQASCRLA (SEQ ID NO: 14), and KK, however the amino acid sequence is not limited to the above-described examples. In one exemplary embodiment, the polypeptide substrate 13a may be PLGVRG (-Pro-Leu-Gly-Val-Arg-Gly-; SEQ ID NO: 15) which can be specifically degraded by MMP2, or LR (-Leu-Arg-) which can be specifically degraded by cathepsin S.

The backbone 13 is disposed between and chemically bonded to the metal nanoparticle 11 and the photosensitizer 15. Here, the polypeptide substrate 13a itself may be chemically bonded to the metal nanoparticle 11 and the photosensitizer 15. The backbone 13 may further include at least one of a first linker 13b chemically linking the polypeptide substrate 13a with the metal nanoparticle 11, and a second linker 13c chemically linking the polypeptide substrate 13a with the photosensitizer 15. In one example, the metal nanoparticle 11 and/or the photosensitizer 15 may be bonded to a side chain of the backbone 13.

Specifically, the backbone 13 may be chemically adsorbed to the metal nanoparticle 11, and covalently bonded to the photosensitizer 15. In one example, the first linker 13b may be linked with the polypeptide substrate 13a by a peptide bond, and linked with a surface of the metal nanoparticle 11 by a thiol-metal bond. To this end, the first linker 13b may be cysteine having a thiol group on a side chain, a polypeptide having cysteine, or alkylene having an amino or carboxyl group on a main chain (or a side chain) and a thiol group on a side chain (or a main chain). The second linker 13c may be linked with the polypeptide substrate 13a by a peptide bond, and linked with the photosensitizer 15 by an amide bond. To this end, the second linker 13c may be lysine having an amino group on a side chain, a polypeptide having lysine, or alkyl or alkylene having amino groups on a side chain and/or a main chain. The photosensitizer 15 has a carboxyl group as a substituent, which may form an amide bond by reaction with an amino group of the second linker 13c. However, the present invention is not limited thereto. When one terminal amino acid of the polypeptide substrate 13a is cysteine, the first linker 13b may be omitted, and when the other terminal amino acid of the polypeptide substrate 13a is lysine, the second linker 13c may be omitted.

The backbone 13 may have the appropriate number of amino acids, which constitute the backbone 13, or the appropriate number of carbon atoms of an alkylene group such that the photosensitizer 15 is spaced within about 20 nm from the surface of the metal nanoparticle 11.

The photosensitizer 15 may be a porphyrin-based compound or a non-porphyrin compound, the compound may be in the form of a free base or metal complex. Examples of the porphyrin-based compound may include porphyrin derivatives; reduced porphyrins, in which at least one pyrrole constituting porphyrin is reduced into pyrroline, such as chlorin and bacteriochlorin; and porphyrin analogues such as phthalocyanine and naphthalocyanine Examples of the non-porphyrin compound may include hypericin, rhodamine, rose Bengal, psoralen, phenothiazinium-series dye, or merocyanine.

The photosensitizer 15 is non-toxic in a ground energy state, whereas it is excited to a singlet energy state when light having a specific wavelength is absorbed. Majority of the photosensitizers in the singlet excited state transit to a triplet excited state through intersystem crossing, and others return to the ground energy state by emitting their energy in the form of fluorescence. The photosensitizer in the singlet or triplet excited state produces reactive oxygen species such as singlet oxygen, oxygen radical, super oxide or peroxide, by reaction with a surrounding substrate or oxygen. The produced reactive oxygen species may result in apoptosis or necrosis of surrounding tumor cells.

In consideration of light penetration capability into a tissue and production efficiency of the reactive oxygen species, the photosensitizer 15 may be a material excited by light having a wavelength of 450 to 950 nm, and preferably, 600 to 900 nm.

The metal nanoparticle 11 is a nanoparticle at least having a length extending in one direction of several to several tens of nanometers, which may contain a metal capable of performing resonance energy transfer with the photosensitizer 15. The metal contained in the metal nanoparticle 11 may be gold (Au), silver (Ag), copper (Cu), platinum (Pt), palladium (Pd), nickel (Ni), iron (Fe) or a combination of at least two thereof. Specifically, when the photosensitizer-metal nanoparticle complex 10 in which the metal nanoparticle 11 is linked with the photosensitizer 15 by the backbone 13 is exposed to light having a specific wavelength, energy transfer may occur to the surface of the metal nanoparticle 11 from the photosensitizer 15 in the singlet excited state, and thus the photosensitizer 15 is not only unable to emit fluorescence, but also cannot produce reactive oxygen species. As a result, the photosensitizer-metal nanoparticle complex 10 in which the metal nanoparticle 11 is linked with the photosensitizer 15 by the backbone 13 cannot have cytotoxicity.

In one exemplary embodiment, the metal contained in the metal nanoparticle 11 may be Au, which has a molar absorption coefficient of $10^9$ or more, thereby effectively absorbing light 10000 times more than the photosensitizer 15, and facilitates material introduction to a surface. The metal nanoparticle 11 may have the form of a sphere, rod, pyramid, star, or core-shell. The light absorption spectrum of the metal nanoparticle 11 may be various depending on its components, shape or size. Thus, to overlap a fluorescence spectrum of the photosensitizer 15 with a light absorption spectrum of the metal nanoparticle 11, the components, shape or size of the metal nanoparticle 11 may be adjusted.

A hydrophilic polymer 17 may be further linked to a terminal of the backbone 13, specifically, the terminal adjacent to the photosensitizer 15. The hydrophilic polymer may be poly(alkylene glycol) having biocompatibility such as low immunogenicity. The poly(alkylene glycol) may be polyethylene glycol (PEG); methoxy polyethylene glycol (MPEG); methoxy polypropylene glycol; a copolymer of PEG and methoxy polypropylene glycol; dextran; hyaluronic acid; a copolymer of polylactic acid and polyglycolic acid; PEG-diacid; PEG monoamine; MPEG monoamine; MPEG hydrazide; MPEG imidazole; or a copolymer of at least two selected from the group consisting of PEG, methoxy polypropylene glycol, PEG-diacid, PEG monoamine, MPEG monoamine, MPEG hydrazide, and MPEG imidazole. Alternatively, the hydrophilic polymer may be a copolymer of poly(alkylene glycol) and another polymer, such as a copolymer of PEG and polypeptide, PEG and polysaccharide, PEG and polyamidoamine, PEG and polyethyleneimine, or PEG and polynucleotide.

An example of the photosensitizer-metal nanoparticle complex 10 may be represented by Formula 1 below:

("Pro-Leu-Gly-Val-Arg-Gly" disclosed as SEQ ID NO: 15)

40

Figure 2:
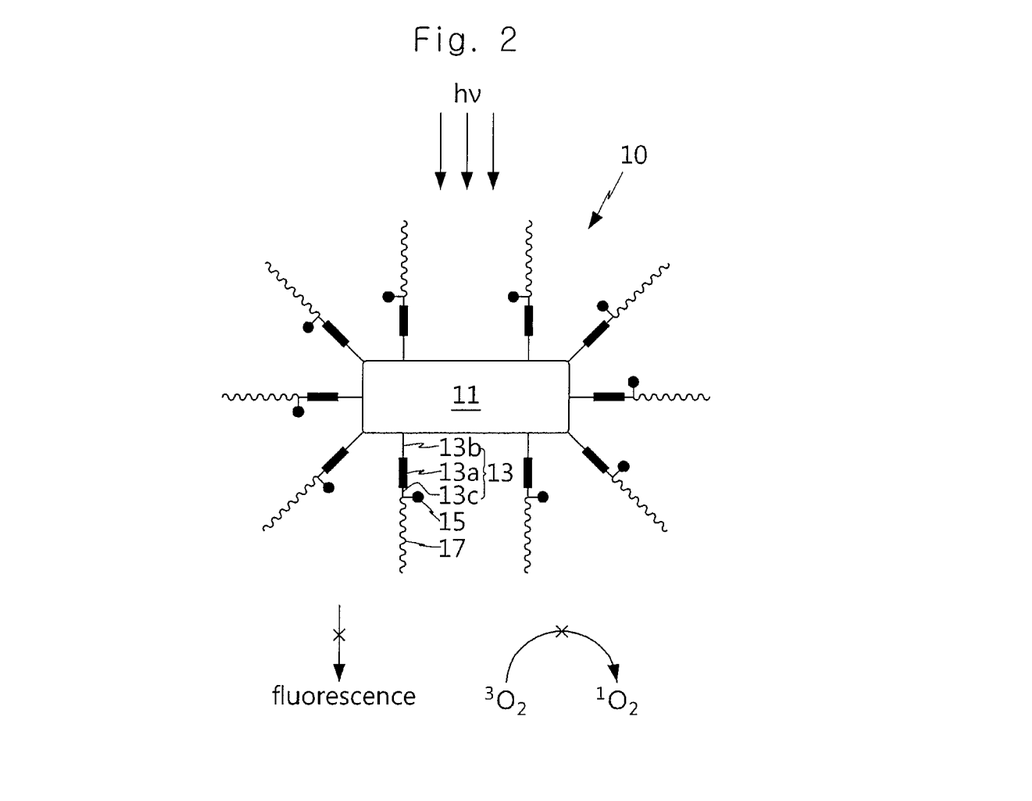
FIGS. 2 and 3 are schematic views illustrating light-induced reactions of photosensitizer-metal nanoparticle complexes accumulated in a normal tissue and the lesion in which a protease is overexpressed, according to an exemplary embodiment of the present invention, respectively.
Figure 3:
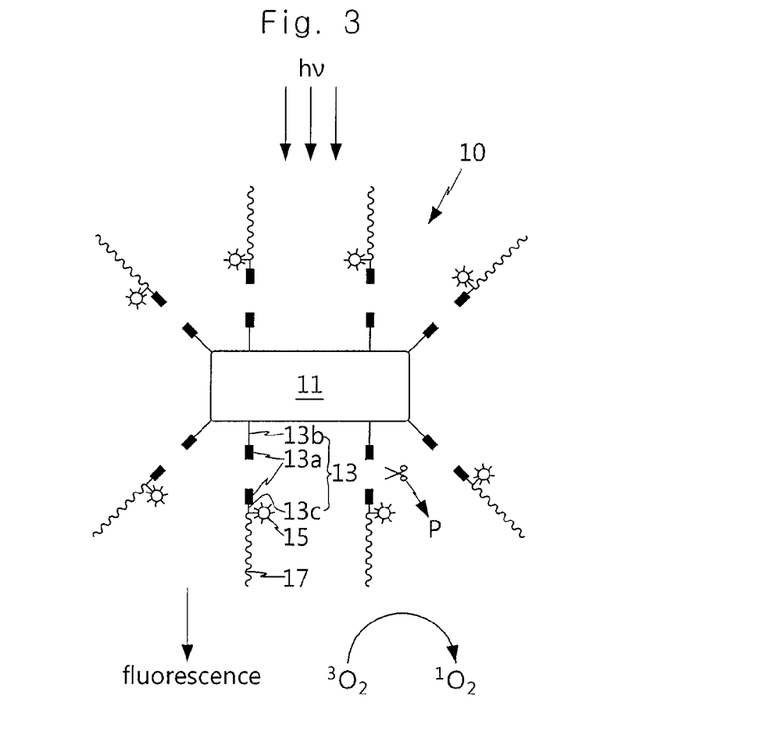

FIGS. 2 and 3 are schematic views illustrating light-induced reactions of the photosensitive-metal nanoparticle complexes accumulated in a normal tissue and the lesion in which a protease is overexpressed, according to an exemplary embodiment of the present invention, respectively.

Referring to FIG. 2, the photosensitizer-metal nanoparticle complex 10 accumulated in the normal tissue maintains the linkage between the metal nanoparticle 11 and the photosensitizer 15 by the backbone 13. Thus, when the complex 10 is exposed to light having a wavelength capable of exciting the photosensitizer 15, energy transfer to the surface of the metal nanoparticle 11 from the photosensitizer 15 in the singlet excited state, that is, resonance energy transfer, may occur. In this case, the metal nanoparticle 11 may serve as a quencher to inhibit fluorescence of the photosensitizer 15 and production of reactive oxygen species. As a result, the complex 10 cannot have cytotoxicity.

Referring to FIG. 3, the photosensitizer-metal nanoparticle complex 10 accumulated in the lesion meets a protease P overexpressed in the infected tissue, and the protease P specifically degrades the polypeptide substrate 13a in the backbone 13 of the complex 10, thereby separating the metal nanoparticle 11 and the photosensitizer 15 from each other. As a result, a distance between the surface of the metal nanoparticle 11 and the photosensitizer 15 exceeds a distance in which resonance energy transfer can be occurred, for example, 20 nm. Afterwards, when the complex 10 is exposed to light having a wavelength capable of exciting the photosensitizer 15, the photosensitizer 15 is excited to a singlet state. Majority of the photosensitizers in the singlet excited state transit to a triplet excited state through intersystem crossing, and others return to a ground state by emitting energy in the form of fluorescence. The singlet or triplet-state photosensitizer produces reactive oxygen species such as singlet oxygen, oxygen radical, super oxide, or peroxide by reaction with a surrounding substrate or oxygen. The produced reactive oxygen species may result in the apoptosis or necrosis of surrounding tumor cells.

Meanwhile, when the photosensitizer-metal nanoparticle complex 10 is administered to a living body having a tumor, the nano-sized complex 10 is easily penetrated into the tumor due to a newly-formed leaky blood vessel existing in the tumor, and accumulated in the tumor due to a lack of excretion through a lymphatic vessel and thus remains in the tumor for a long time. However, it is possible for the complex 10 to be non-specifically accumulated in normal tissues such as eyes or skin.

However, a protease is overexpressed in the tumor more than in the normal tissues. For this reason, as described with reference to FIG. 2, since the complex 10 maintains the linkage of the photosensitizer 15 and the metal nanoparticle 11 by the backbone 13 in the normal tissues, even when the complex 10 is exposed to light having a wavelength capable of exciting the photosensitizer 15, the fluorescence and the production of reactive oxygen species can be inhibited. However, as described with reference to FIG. 3, since the photosensitizer 15 may be separated from the metal nanoparticle 11 in the tumor by the protease, when the complex 10 is exposed to light having a wavelength capable of exciting the photosensitizer 15, the fluorescence and the production of reactive oxygen species may be activated. As a result, a photosensitive reaction can be inhibited in the normal tissues, and the tumor tissues can be effectively destroyed. In addition, selective fluorescence in the tumor tissues may further improve accuracy of tumor diagnosis using the complex.

Pharmaceutical Composition containing Photosensitizer-Metal Nanoparticle Complex In still another exemplary embodiment of the present invention, a pharmaceutical composition containing a photosensitizer-metal nanoparticle complex described with reference to FIG. 1 is provided.

The pharmaceutical composition according to the exemplary embodiment includes a pharmaceutically effective amount of the photosensitizer-metal nanoparticle complex, and a pharmaceutically available carrier. The carrier may be a diluent. The composition may further include an additive, such as a preservative, a wetting agent, an emulsifier, or a dispersing agent.

Such a pharmaceutical composition may be formulated in accordance with a desired administration route. Examples of the administration route may include, but are not limited to, non-oral administrations, including intravenous, intradermal, subcutaneous, intranasal, percutaneous (local), transmucosal and rectal administrations.

Proper carriers capable of being used for non-oral administrations are well known to those ordinarily skilled in the art. Examples of the carrier may include aqueous vehicles including, but not limited to, an injectable solution containing sodium nitride, a Ringer's solution, an injectable solution containing dextrose, an injectable solution containing dextrose and sodium nitride, and a Ringer's solution containing lactate; water-miscible vehicles including, but not limited to, ethyl alcohol, PEG, and polypropylene glycol; and non-aqueous vehicles including, but not limited to, corn oil, cottonseed oil, peanut oil, sesame oil, ethyl oleate, isopropyl myristate, and benzyl benzoate.

Such a pharmaceutical composition may be used to treat or diagnose a tumor. When used to treat or diagnose a tumor, an effective amount may be determined by a physician depending on cases. Here, a patient's age, sex, weight, or severity of the disease to be treated or diagnosed may be considered. As one example, the photosensitizer-metal nanoparticle complex may be administered in an amount of 0.001 μg to 10 mg per kilogram based on an equivalent weight of the photosensitizer and the weight of the patient. In a specific example, the complex may be administered in an amount of 0.1 to 1 mg/kg.

EXAMPLES

Hereinafter, exemplary examples will be disclosed to help understanding of the present invention. However, the exemplary examples are merely to explain the present invention, and not to limit the scope of the present invention.

Preparation Example 1

Preparation of Metal Nanoparticle

A metal nanoparticle was prepared using a seed-mediated method. Specifically, cetyltrimethylammonium bromide (CTAB) was dissolved in tertiary distilled water to a molarity of 100 mM, thereby preparing CTAB aqueous solution. 7.5 ml of the CTAB aqueous solution was mixed with 250 μl of 10 mM $HAuCl_4$ aqueous solution ($HAuCl_4.3H_2O$), and then 600 μl of 10 mM $NaBH_4$ aqueous solution was added. The mixture was stirred for 2 minutes, and maintained at 25° C. for 2 hours to prepare a seed solution.

Meanwhile, 1.7 ml of 10 mM $HAuCl_4$ aqueous solution ($HAuCl_4.3H_2O$) was added to 40 ml of 100 mM CTAB aqueous solution, and 250 μl of 10 mM $AgNO_3$ aqueous solution and 270 μl of 100 mM ascorbic acid were sequentially added. Here, 420 μl of the seed solution was added, and then maintained to react for 12 hours. Afterwards, the reaction mixture was centrifuged at 15000 g, 25° C. for 15 minutes, thereby obtaining a gold nanorod.

Figure 4:
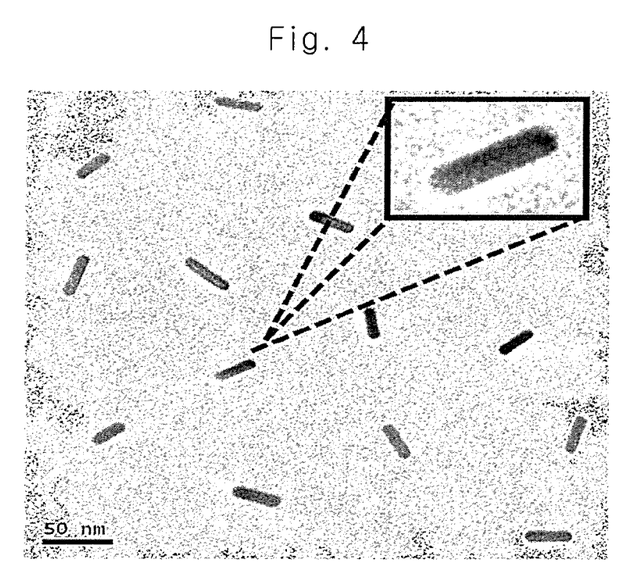
FIG. 4 is a transmission electron microscope (TEM) photograph of a gold nanorod prepared in Preparation Example 1.

FIG. 4 is a transmission electron microscope (TEM) photograph of the gold nanorod prepared in Preparation Example 1.

Referring to FIG. 4, it can be seen that a gold nanorod having an average length of 34 nm and a width of 9 nm was formed.

Preparation Example 2

Preparation of Photosensitizer-Polypeptide Conjugate (MMP2 Probe)

("Cys-Gly-Gly-Pro-Leu-Gly-Val-Arg-Gly-Lys" disclosed as SEQ ID NO: 16)

(2)

↓ (Boc)₂O, DIPEA, DMF

A compound (2) was obtained through typical solid-phase synthesis using a rink amide MBHA resin as a solid support, Fmoc-mini-PEG™ (9-fluorenylmethoxycarbonyl-8-amino-3,6-dioxaoctanoic acid, available from PEPNET), and amino acids in which an amino group is protected by a Fmoc (fluorenylmethoxycarbonyl) group. Specifically, the compound (2) was obtained by repeating sequential operations of (a) deprotecting Fmoc using a 20% piperidine/dimethylformamide (DMF) solution, (b) adding Fmoc-mini-PEG™, and (c) performing carboxyl acid activation and coupling using a DMF solution containing N,N-diisopropylethylamine (DIPEA), hydroxybenzotriazole (HOBt), and O-(benzotriazol-1-yl)-N,N,N',N'-tetramethyluronium hexafluorophosphate (HBTU), four times; and then repeating sequential operations of (d) deprotecting Fmoc using a 20% piperidine/DMF solution, (e) adding Fmoc-amino acids, and (f) performing carboxyl acid activation and coupling using a DMF solution including DIPEA, HOBt, and HBTU, for ten times. Here, the Fmoc-amino acids sequentially added were Fmoc-Lys (Alloc) which was a lysine having a residue protected by an allyloxycarbonyl (Alloc) group, Fmoc-Gly, Fmoc-Arg(Pbf) which was an arginine having a residue protected by a pentamethyldihydro-benzofuran-5-sulfonyl) (Pbf) group, Fmoc-Val, Fmoc-Gly, Fmoc-Leu, Fmoc-Pro, Fmoc-Gly, Fmoc-Gly, and Fmoc-Cys(Trt) which was a cysteine having a residue protected by a trityl (Trt) group.

A terminal amino group of the compound (2) was substituted with a t-butoxycarbonyl (Boc) group by adding a DMF solution including (Boc)$_2$O and DIPEA to the compound (2), thereby obtaining a compound (3). Afterwards, Alloc protecting the lysine residue of the compound (3) was deprotected by adding a methylene chloride (MC) solution including Tetrakis(triphenylphosphine)palladium(0) (Pd(PPh$_3$)$_4$) and 1,3-dimethylbarbituric acid to the compound (3), thereby obtaining a compound (4). Then, the compound (4) was coupled with pyropheophorbide a (ppa) by adding a DMF solution including ppa, DIPEA, HOBt, and HBTU to the compound (4), thereby obtaining a compound (5). A mixture formed of trifluoroacetic acid (TFA), triisopropylsilane (TIS), 1,2-ethanedithiol (EDT), thioanisole, and water in a volume ratio of 90:2.5:2.5:2.5:2.5 was added to the compound (5), thereby obtaining a mixed solution by cutting off a compound (6) from the rink amide MBHA resin.

An excessive amount of a diethylether solvent was treated to the obtained mixed solution to produce a precipitate. Centrifugation to completely precipitate the mixed solution and removal of excessive TFA, TIS, EDT, thioniasole and so on were performed twice, thereby obtaining a solidified precipitate. The obtained precipitate was purified using high performance liquid chromatography (HPLC). The purified material product was freeze-dried, thereby yielding a photosensitizer-polypeptide conjugate as the compound (6), that is, an MMP2 probe (MMP2P). PLGVRG (-Pro-Leu-Gly-Val-Arg-Gly-) peptide sequence (SEQ ID NO: 15) in the MMP2 probe was introduced as the substrate for enzymatic hydrolysis by matrix metalloproteinase 2 (MMP2).

Figure 5:
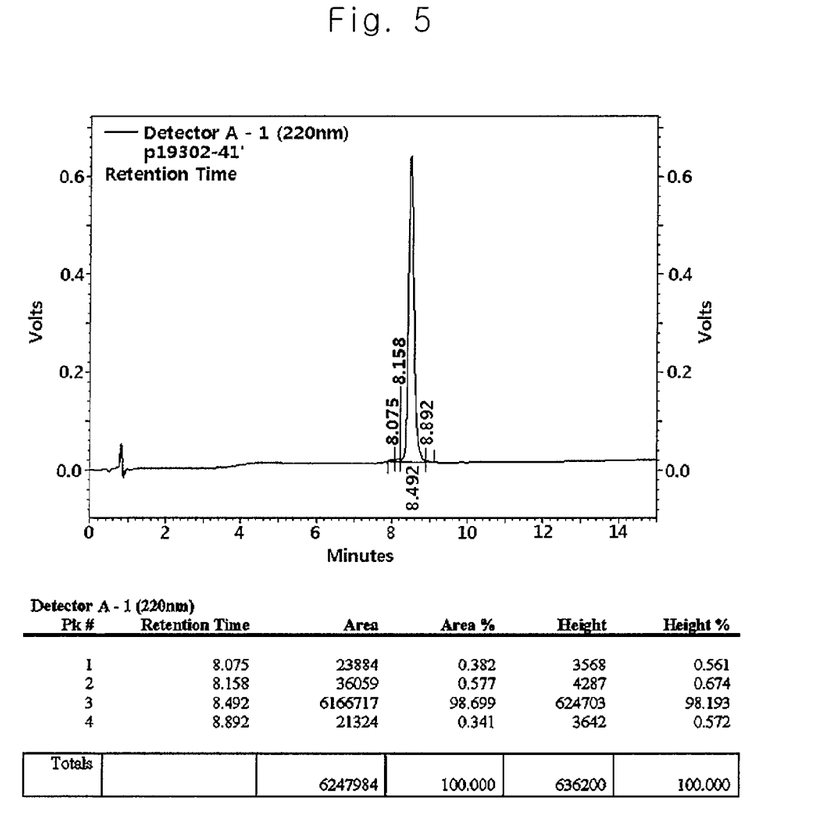
FIG. 5 shows an HPLC result for an MMP2 probe prepared in Preparation Example 2.
Figure 6:
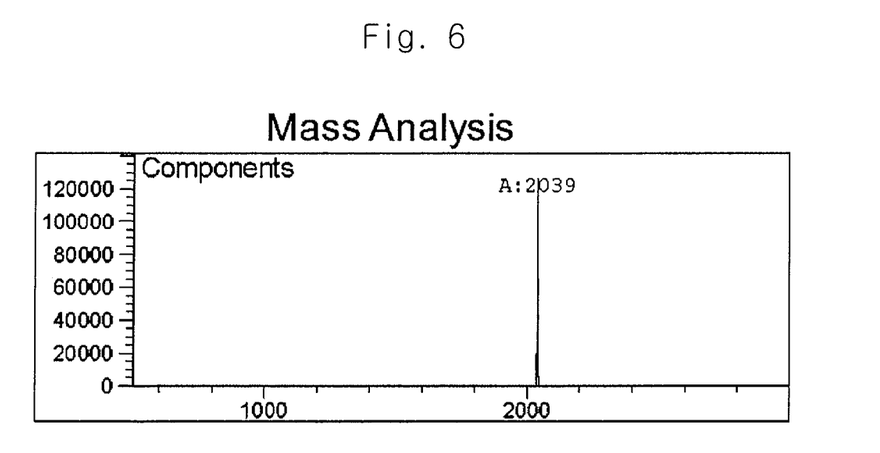
FIG. 6 shows the results of mass analysis for the MMP2 probe prepared in Preparation Example 2.

FIG. 5 shows an HPLC result for the MMP2 probe prepared in Preparation Example 2, and FIG. 6 shows results of mass analysis for the MMP2 probe prepared in Preparation Example 2.

Referring to FIGS. 5 and 6, it was identified that the MMP2 probe prepared in Preparation Example 2 had a purity of about 98%, and a molecular weight of 2039 g/mol, indicating production of the compound (6).

Preparation Example 3

Preparation of Photosensitizer-Metal Nanoparticle Complex (MMP2P-GNR)

The gold nanorod prepared in Preparation Example 1 was put into 1 ml of distilled water to prepare a gold nanorod dispersion having a concentration of 100 nM. 200 µl of aqueous solution prepared by dissolving the MMP2 probe prepared in Preparation Example 2 to a concentration of 1 mM and 100 µl of 2 mM $K_2CO_3$ aqueous solution were added to the dispersion to react at room temperature for 5 days. The resulting solution was dialyzed in distilled water using an ultrafiltration membrane having a molecular weight cut off (MWCO) of 50000 to remove MMP2 probes that did not participate in the reaction with the gold nanorod, thereby obtaining a solution of photosensitizer-metal nanoparticle complex in which the photosensitizer-polypeptide combination was linked with the gold nanorod, that is, MMP2P-GNR.

Figure 7:
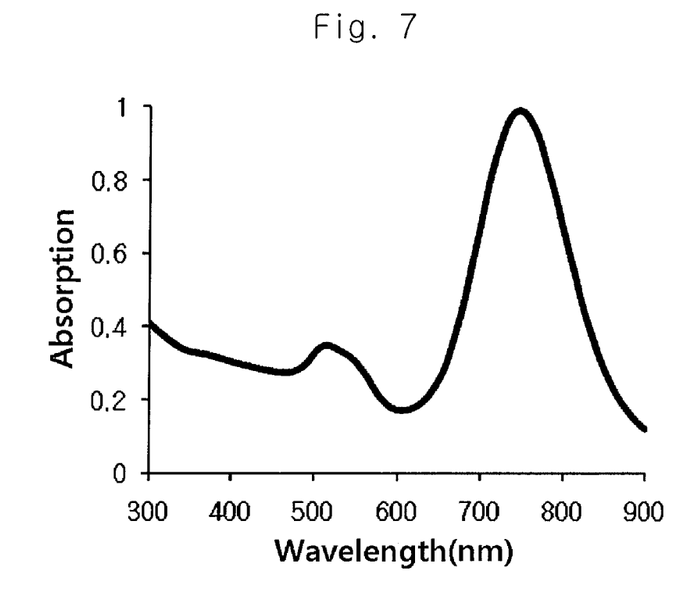
FIG. 7 shows a UV/Vis absorption spectrum of the gold nanorod according to Preparation Example 1.

FIG. 7 shows a UV/Vis absorption spectrum of the gold nanorods prepared in Preparation Example 1.

Referring to FIG. 7, it can be seen that the maximum absorption wavelength was about 750 nm, and a strong absorption spectrum was observed in a fluorescence wavelength of ppa, i.e., 650 to 780 nm.

Figure 8:
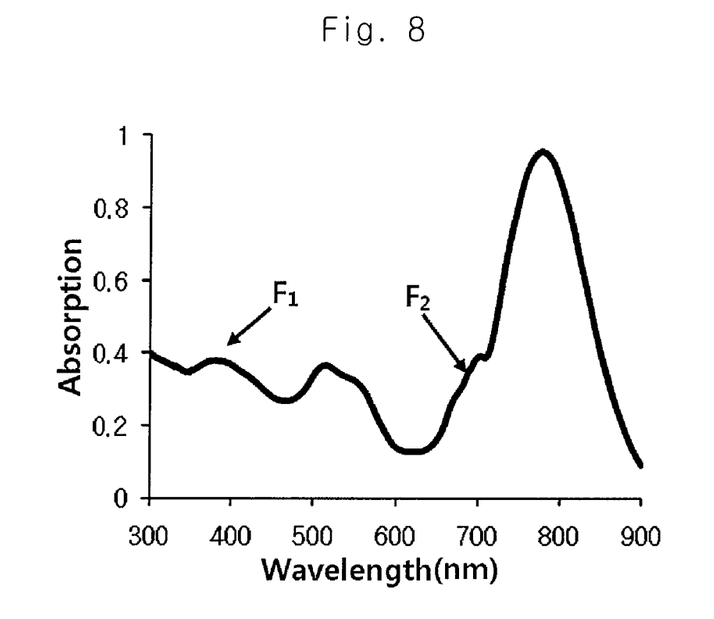
FIG. 8 shows a UV/Vis absorption spectrum of a photosensitizer-metal nanoparticle complex according to Preparation Example 2.

FIG. 8 shows a UV/Vis absorption spectrum of the photosensitizer-metal nanoparticle complex (MMP2P-GNR) prepared in Preparation Example 3.

Referring to FIGS. 7 and 8, compared to the UV/Vis absorption spectrum of the gold nanorod prepared in Preparation Example 1 (FIG. 7), the UV/Vis absorption spectrum of the photosensitizer-metal nanoparticle complex prepared in Preparation Example 3 (FIG. 8) showed additional absorption peaks at 387 nm (F1, Soret band) and 670 nm ($F_2$, Q band), which are absorption peaks by the photosensitizer. From the analysis of the UV/Vis absorption spectrum of FIG. 8, it can be identified that a concentration of the photosensitizer in the solution of the photosensitizer-metal nanoparticle complex obtained by the dialysis was 75 µM equivalent weight.

Analysis Example 1

Analysis of Fluorescence Activation in Photosensitizer-Metal Nanoparticle Complex (MMP2P-GNR)

HT1080 cells (human fibrosarcoma cell line) overexpressing MMP2 and BT20 cells (human mammary adenocarcinoma cell line) underexpressing MMP2 (see Bremer C. et al., Nature Medicine 7(6) 743-748, 2001) were obtained from ATCC (Manassas, Va.). MMP2-positive HT1080 (90,000 cells) and MMP2-negative BT20 cells (90,000 cells) in culture media were seeded into each wells of LabTek II Chambered Coverglass. Afterwards, the photosensitizer-metal nanoparticle complex solution prepared in Preparation Example 2 was diluted with a culture medium to have 5 µM equivalent weight of the photosensitizer, and added at 600 µl per well. The cells were incubated in an incubator at 37° C. for 15 hours. After the culture medium including the complex was removed, and the cells were washed three times with a fresh culture medium, fluorescence was observed using a confocal microscope (Ex. 405 nm, Em. 646-753 nm).

Figure 9:
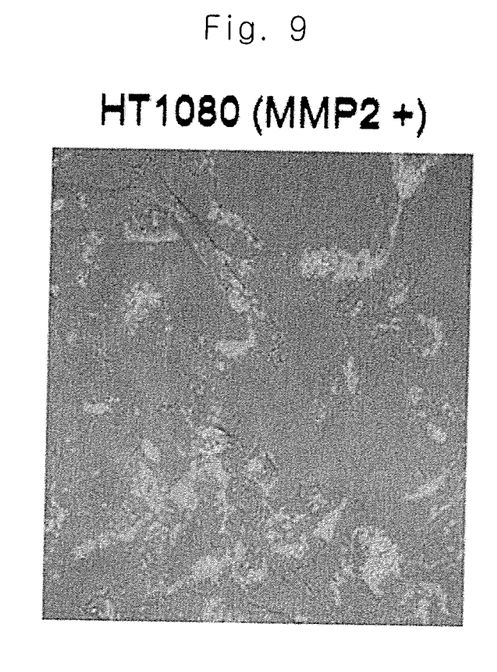
FIGS. 9 and 10 are photographs showing fluorescence in cell lines HT1080 and BT20 treated with photosensitizer-metal nanoparticle complexes, respectively.
Figure 10:
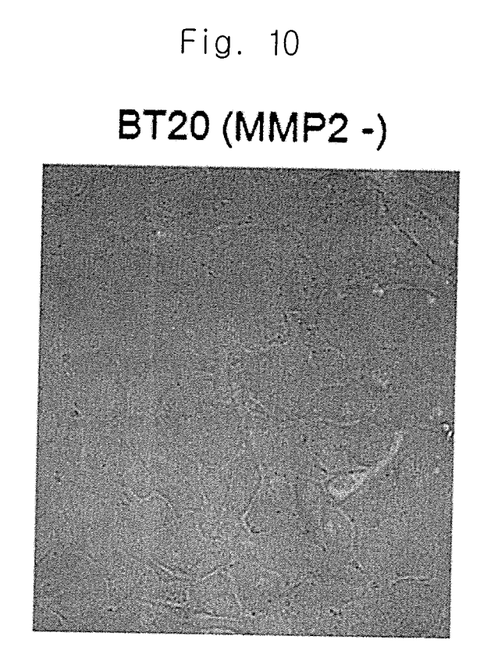

FIGS. 9 and 10 are photographs showing fluorescence in cell lines HT1080 and BT20 treated with photosensitizer-metal nanoparticle complexes, respectively.

Referring to FIGS. 9 and 10, it can be seen that, compared with the cell line BT20 underexpressing MMP2, the cancer cell line HT1080 overexpressing MMP2 exhibited a much stronger fluorescence. From the result, it can be noted that when a polypeptide of the photosensitizer-metal nanoparticle complex was degraded by the MMP2, the photosenstizer was separated from the metal nanoparticle, and the separated photosensitizer exhibited strong fluorescence. Thus, it can also be noted that when the photosensitizer-metal nanoparticle complex is administered to a patient, and fluorescence following light radiation is detected, a location of the tissue in which MMP2 is overexpressed can be more exactly diagnosed.

Analysis Example 2

Analysis of Cell Viability after Photodynamic Therapy

Analysis Example 2-1

Analysis on Cell Line HT1080

For in vitro phototoxicity tests 9,000 HT1080 cells were seeded in each well of 96-well plates. The next day, the photosensitizer-polypeptide conjugate (MMP2P) prepared in Preparation Example 2 and the photosensitizer-metal nanoparticle complex (MMP2P-GNR) prepared in Preparation Example 3 were diluted with a cell culture medium, respectively, thereby preparing an MMP2 probe (MMP2P) solution and a photosensitizer-metal nanoparticle complex (MMP2P-GNR) solution, each of which has a final concentration corresponding to 5 µM equivalent weight of the photosensitizer. Each solution was added at 200 µl per well to some wells, and the plate was maintained at 37° C. for 15 hours. Meanwhile, for the control group, the same volume of a fresh culture medium in which the photosensitizer is not included was added to the other wells. Afterwards, the cells were washed twice with a cell culture medium, and for a photodynamic therapy (PDT) group, photodynamic therapy was carried out using laser at 670 nm under conditions including a dose density of 40 mW/cm$^2$ and a dose of 10 J/cm$^2$. After 24 hours, cell viability was measured by MTT analysis.

Analysis Example 2-2

Analysis on Cell Line BT20

9,000 BT20 cells were seeded in each well of 96-well plates. The next day, the photosensitizer-polypeptide conjugate prepared in Preparation Example 2 and the photosensitizer-metal nanoparticle complex prepared in Preparation Example 2 were diluted with a cell culture medium, thereby preparing an MMP2 probe (MMP2P) solution and a photosensitizer-metal nanoparticle complex (MMP2P-GNR) solution, which have a final concentration corresponding to 5 µM equivalent weight of the photosensitizer. Each solution was added at 200 µl per well to some wells, and the plate was maintained at 37° C. for 15 hours. Meanwhile, for the control group, the same volume of a fresh culture medium in which the photosensitizer was not included was added. Afterwards, the cells were washed twice with a cell culture medium, and for a photodynamic therapy (PDT) group, photodynamic therapy was performed using laser at 670 nm under conditions including a light dose density of 40 mW/cm$^2$, and a light dose of 10 J/cm$^2$. After 24 hours, cell viability was measured by MTT analysis.

In Table 1, conditions for each group analyzed in Analysis Example 2-1 or 2-2 are shown.

TABLE 1

| Cell Line | Type | Conditions | |
|---|---|---|---|
| | | Treatment for Cell Line | Photodynamic Therapy |
| HT1080 | Media Control | Cell culture medium | No |
| | (MMP2P-GNR)-PDT | Photosensitizer-metal nanoparticle complex | No |
| | (MMP2P)-PDT | Photosensitizer-polypeptide conjugate | No |
| | (MMP2P-GNR) + PDT | Photosensitizer-metal nanoparticle complex | Yes |
| | (MMP2P) + PDT | Photosensitizer-polypeptide conjugate | Yes |
| BT20 | Media Control | Cell culture medium | No |
| | (MMP2P-GNR)-PDT | Photosensitizer-metal nanoparticle complex | No |
| | (MMP2P)-PDT | Photosensitizer-polypeptide conjugate | No |
| | (MMP2P-GNR) + PDT | Photosensitizer-metal nanoparticle complex | Yes |
| | (MMP2P) + PDT | Photosensitizer-polypeptide conjugate | Yes |

Figure 11:
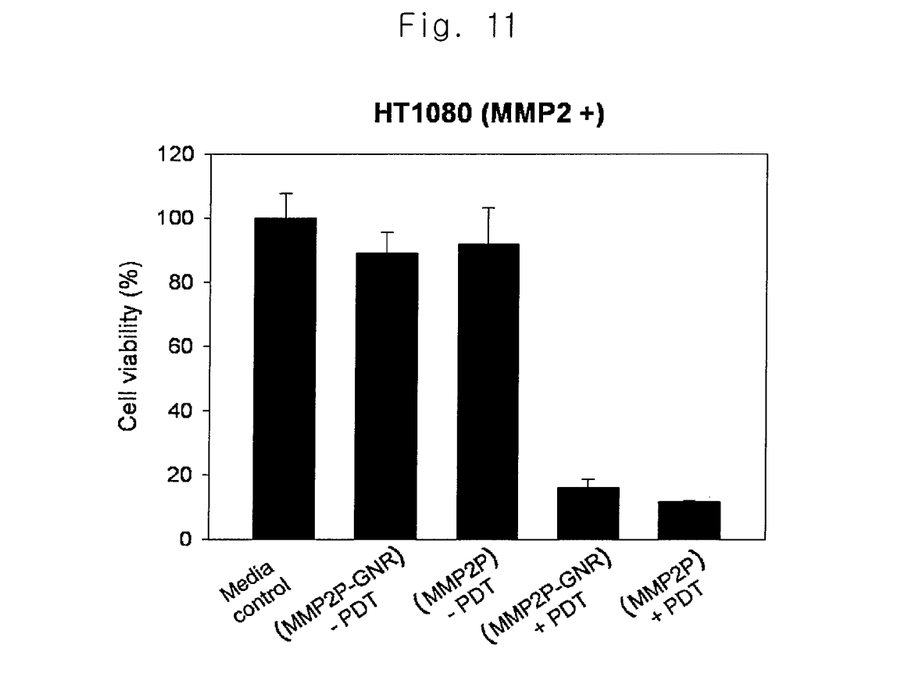
FIGS. 11 and 12 are graphs of cell viability based on conditions in Analysis Examples 2-1 and 2-2, respectively.
Figure 12:
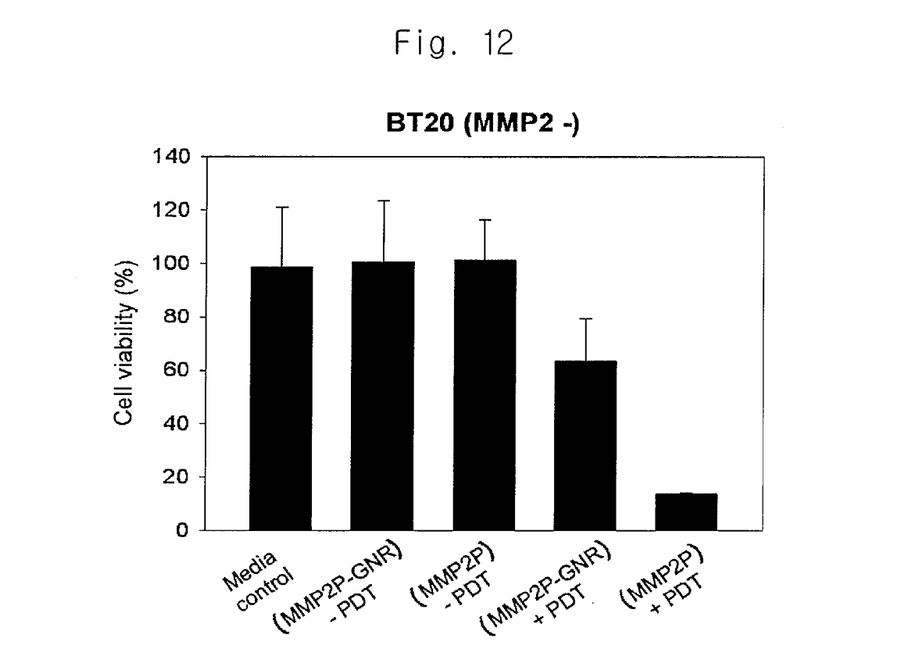

FIGS. 11 and 12 are graphs of cell viability depending on the conditions in Analysis Examples 2-1 and 2-2, respectively.

Referring to FIGS. 11 and 12, it can be seen that when the photosensitizer-polypeptide conjugate was treated, and the photodynamic therapy was carried out (MMP2P+PDT), both the cell lines HT1080 and BT20 exhibited low cell viabilities, and thus had high phototoxicity. However, when the photosensitizer-metal nanoparticle complex in which the photosensitizer-polypeptide conjugate was coupled to the metal nanoparticle was treated, and the photodynamic therapy was carried out (MMP2P-GNR+PDT), the cell line HT1080 exhibited a cell viability of 16%, whereas the cell line BT20 exhibited a cell viability of 63%. Accordingly, it can be seen that the phototoxicity induced by the photosensitizer-metal nanoparticle complex was selectively activated by MMP2. In other words, it can be noted that the photosensitizer-metal nanoparticle complex has phototoxicity only in tissues in which MMP2 is overexpressed, and does not have phototoxicity in tissues in which MMP2 is underexpressed, that is, normal tissues. As a result, when the photosensitizer-metal nanoparticle complex is administered to a patient, and then the photodynamic therapy is carried out, only the tissues in which MMP2 is overexpressed can be selectively treated.

While the invention has been shown and described with reference to certain exemplary embodiments thereof, it will be understood by those skilled in the art that various changes in form and details may be made therein without departing from the spirit and scope of the invention as defined by the appended claims.

The invention claimed is:

1. A photosensitizer-metal nanoparticle complex, which is represented by the following Formula ("Pro-Leu-Gly-Val-Arg-Gly-Lys" disclosed as SEQ ID NO: 17):

$$NH_2-CH(CH_2-S-M)-C(=O)-NH-CH_2-C(=O)-NH-CH_2-C(=O)-$$

$$-\text{Pro-Leu-Gly-Val-Arg-Gly-Lys}-(NH-CH_2-CH_2-O-CH_2-CH_2-O-CH_2-C(=O))_4-NH_2$$
$$|$$
$$PS$$

wherein M is a metal nanoparticle, PS is a photosensitizer having a carboxyl group, and
the lysine (Lys) is linked with the photosensitizer by an amide bond.

2. The complex according to claim 1, wherein the photosensitizer is a porphyrin-based compound or a non-porphyrin compound in the form of a free base or metal complex.

3. The complex according to claim 2, wherein the photosensitizer is pyropheophorbide a.

4. The complex according to claim 1, wherein the metal nanoparticle has gold, silver, copper, platinum, palladium, nickel, iron, or a combination of at least two thereof.

5. The complex according to claim 1, wherein the metal nanoparticle is a gold nanoparticle.

6. The complex according to claim 1, wherein the metal nanoparticle has the form of a sphere, rod, pyramid, star, or core-shell.

7. A composition for photodynamic therapy or diagnosis, comprising a photosensitizer-metal nanoparticle complex according to claim 1 and a pharmaceutically available carrier.

8. A photosensitizer-metal nanoparticle complex, which is represented by Formula 1 ("Pro-Leu-Gly-Val-Arg-Gly" disclosed as SEQ ID NO: 15):

[Formula 1]

* * * * *

SEQUENCE LISTING

```
<160> NUMBER OF SEQ ID NOS: 17

<210> SEQ ID NO 1
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide substrate

<400> SEQUENCE: 1

Arg Pro Leu Ala Leu Trp Arg Ser
1               5

<210> SEQ ID NO 2
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide substrate

<400> SEQUENCE: 2

Gly Gly Leu Gly Gln Arg Gly Arg Ser Ala Asn Ala Ile Leu Glu
1               5                   10                  15

<210> SEQ ID NO 3
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide substrate

<400> SEQUENCE: 3

Gly Val Ser Gln Asn Tyr Pro Ile Val Gly
1               5                   10
```

<210> SEQ ID NO 4
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide substrate

<400> SEQUENCE: 4

Leu Val Leu Ala Ser Ser Ser Phe Gly Tyr
1               5                   10

<210> SEQ ID NO 5
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide substrate

<400> SEQUENCE: 5

Pro Leu Gly Met Trp Ser Arg
1               5

<210> SEQ ID NO 6
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide substrate

<400> SEQUENCE: 6

Pro Gly Asn Trp Thr
1               5

<210> SEQ ID NO 7
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide substrate

<400> SEQUENCE: 7

Pro Ala Gly Leu Leu Gly Cys
1               5

<210> SEQ ID NO 8
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide substrate

<400> SEQUENCE: 8

Leu Gly Gly Ser Gly Arg Ser Ala Asn Ala Ile Leu Glu
1               5                   10

<210> SEQ ID NO 9
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide substrate

```
<400> SEQUENCE: 9

Gly Pro Ile Cys Phe Phe Arg Leu Gly
1               5

<210> SEQ ID NO 10
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide substrate

<400> SEQUENCE: 10

His Ser Ser Lys Leu Gln Gly
1               5

<210> SEQ ID NO 11
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide substrate

<400> SEQUENCE: 11

Pro Ile Cys Phe Phe
1               5

<210> SEQ ID NO 12
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide substrate

<400> SEQUENCE: 12

His Ser Ser Lys Leu Gln
1               5

<210> SEQ ID NO 13
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide substrate
<220> FEATURE:
<221> NAME/KEY: MOD_RES
<222> LOCATION: (2)..(2)
<223> OTHER INFORMATION: Leu or Gln
<220> FEATURE:
<221> NAME/KEY: MOD_RES
<222> LOCATION: (4)..(4)
<223> OTHER INFORMATION: Ile or Leu

<400> SEQUENCE: 13

Pro Xaa Gly Xaa Ala Gly
1               5

<210> SEQ ID NO 14
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide substrate

<400> SEQUENCE: 14
```

```
Gly Val Val Gln Ala Ser Cys Arg Leu Ala
1               5                   10

<210> SEQ ID NO 15
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide substrate

<400> SEQUENCE: 15

Pro Leu Gly Val Arg Gly
1               5

<210> SEQ ID NO 16
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide substrate

<400> SEQUENCE: 16

Cys Gly Gly Pro Leu Gly Val Arg Gly Lys
1               5                   10

<210> SEQ ID NO 17
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide substrate

<400> SEQUENCE: 17

Pro Leu Gly Val Arg Gly Lys
1               5
```